United States Patent [19]

Heykants et al.

[11] Patent Number: 5,691,354
[45] Date of Patent: Nov. 25, 1997

[54] N-[[1-[4-(4-FLUOROPHENOXY)BUTYL]-4-PIPERIDINYL]-N-METHYL-AMINO]-2-BENZOTHIAZOLOLS AS CLASS III ANTIARRHYTHMIC AGENTS

[75] Inventors: Jozef Jan Pieter Heykants, Vosselaar; Marcel Jan Maria Borgers, Oud-Turnhout, both of Belgium; Doris Wilhelm, Neuss, Germany

[73] Assignee: Janssen Pharmaceutica, N.V., Beerse, Belgium

[21] Appl. No.: 549,830

[22] PCT Filed: Jun. 6, 1994

[86] PCT No.: PCT/EP94/01849

§ 371 Date: Nov. 16, 1995

§ 102(e) Date: Nov. 16, 1995

[87] PCT Pub. No.: WO94/29305

PCT Pub. Date: Dec. 22, 1994

[30] Foreign Application Priority Data

Jun. 11, 1993 [EP] European Pat. Off. .............. 93201685

[51] Int. Cl.$^6$ ............... A61K 31/445; A61K 31/425; C07D 417/12
[52] U.S. Cl. ............................................. 514/321; 546/198
[58] Field of Search ............................ 546/198; 514/321

[56] References Cited

U.S. PATENT DOCUMENTS

| | | | |
|---|---|---|---|
| 4,749,702 | 6/1988 | Janssens et al. | 546/83 |
| 4,861,785 | 8/1989 | Stokbroekx et al. | 514/321 |
| 5,010,198 | 4/1991 | Stokbroekx et al. | 546/114 |
| 5,434,168 | 7/1995 | Stokbroekx et al. | 514/321 |

*Primary Examiner*—Ceila Chang
*Attorney, Agent, or Firm*—Charles J. Metz

[57] ABSTRACT

2-[[1-[4-(4-fluorophenoxy)butyl]-4-piperidinyl] methylamino]-benzothiazololes

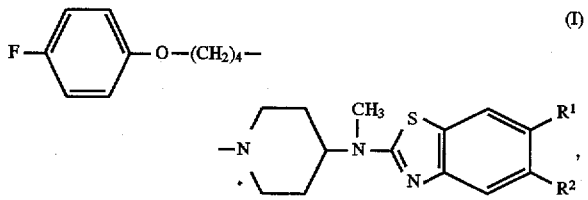

wherein $R^1$ or $R^2$ is hydroxy, the other variable always being hydrogen, and the pharmaceutically acceptable acid addition salts thereof. Novel compounds, pharmaceutical compositions, as well as their use as a class III antiarrhythmicum is disclosed.

4 Claims, No Drawings

N-[[1-[4-(4-FLUOROPHENOXY)BUTYL]-4-PIPERIDINYL]-N-METHYL-AMINO]-2-BENZOTHIAZOLOLS AS CLASS III ANTIARRHYTHMIC AGENTS

CROSS-REFERENCE TO RELATED APPLICATIONS

This application is based upon PCT Application Serial No. PCT/EP 94/01849, filed Jun. 6, 1994, which claims priority from European Patent Application Serial No. 93.201.685.0, filed on Jun. 11, 1993.

The present invention is concerned with novel compounds, i.e. 2-[[1-[4-(4-fluorophenoxy) butyl]-4-piperidinyl]methylamino]-6-benzothiazolol and -5-benzothiazolol, the pharmaceutically acceptable acid addition salts thereof and their use as a class III antiarrhythmic.

Sudden cardiac arrest is a leading cause of death in the Western industrialized world. In the majority of cases sudden death is caused by arrhythmias, more in particular ventricular arrhythmias. (The main cause of these arrythmias is arteriosclerotic coronary artery disease, which narrows or occludes the artery, causing in turn cardiac ischemia and infarction.) Prevention or treatment of arrhythmias could salvage the lives of a large number of individuals who succumb daily to effects of arrhythmias.

Arrhythmias are abnormalities of rate, regularity, or site of origin of the cardiac impulse or a disturbance in conduction through the cardiac tissue, that causes an alteration in the normal sequence of activation of the atria and ventricles. Arrhythmias can roughly be divided into three different types depending upon the intensity of the arrhythmia. A slight form of arrhythmia is the occurrence of premature beats, which are only mild abberations from the normal heart beat. A more intense form of arrhythmia is non-sustained respectively sustained tachycardia, characterized by excessive increase in the contraction frequency of the heart. During said tachycardia the heart still contracts in a coordinated manner, however, the excessive hartfrequency precludes efficient filling of the atria and/or ventricles. Hence, the amount of blood that is circulated throughout the body is severely reduced: obviously a life-threatening situation. The most intense and evidently most dangerous form of arrhythmia is fibrillation or flutter, especially ventricular fibrillation, which is characterized by fibrillation contractions of the heart muscle due to rapid repetitive excitation of heart fibers. Fibrillation or flutter prevents a coordinated contraction of the heart and has, unless immediate medical assistance can be assured, almost always lethal consequences.

Arrhythmias may arise because of abnormalities in either the pulse generation or the pulse conduction in the heart tissue. Most of the already available antiarrhythmic agents have a beneficial effect on the abnormalities in pulse generation. However, for arrhythmias due to abnormalities in pulse conduction, often referred to as reentry arrhythmias, there is still a need for adequate medication (The New England Journal of Medicine, 1991, 324 (12), 781–788). Although drug therapy of cardiac arrhythmias is based on a complex group of considerations, it is generally accepted that an antiarrhythmicum that prolongs the refractory period is among the agents of choice to prevent or treat such reentry arrhythmias. Said antiarrhythmicum capable of prolonging the refractory period is defined according to the Vaughan-Williams classification as a class III antiarrhythmicum (J. Clin. Pharmacology, 1984, 24, 129–147).

In U.S. Pat. No. 4,861,785 there are described compounds having antihypoxic and anti-anoxic properties useful in indications such as shock, cardiac arrest and severe blood loss. Among these compounds features N-[[1-[4-(4-fluorophenoxy)butyl]-4-piperidinyl]-N-methyl-2-benzothiazolamine. Subsequent investigations with this compound have shown it to protect cardiac tissue against ischaemia, reperfusion injury, cardiac glycoside intoxication and $Ca^{2+}$ overload related arrhythmias, which are clearly arrhythmias due to abnormal pulse generation (Cardiovascular Research, 1993, 27,349–357).

Unexpectedly, it has been shown that the structurally related compounds of the present invention are useful as class III antiarrhythmic agents. The present invention is concerned with novel compounds of formula

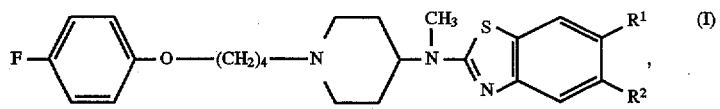

wherein one of the variables $R^1$ and $R^2$ represents hydroxy, while the other variable is hydrogen, and the pharmaceutically acceptable acid addition salts thereof.

The compounds of formula (I) have basic properties and, consequently, they may be converted to their therapeutically active non-toxic acid addition salt forms by treatment with appropriate acids such as, for example, inorganic acids, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methyl-benzenesulfonic, cyclohexanesulfamic, 2-hydroxybenzoic, 4-amino-2-hydroxybenzoic and the like acids. Conversely the salt form can be converted by treatment with alkali into the free base form.

The term acid addition salt as used hereinabove also comprises the solvates which the compounds of formula (I) are able to form and said solvates are meant to be included within the scope of the present invention. Examples of such solvates are e.g. the hydrates, alcoholates and the like.

The compounds of formula (I) are 2-[[1-[4-(4-fluorophenoxy)butyl]-4-piperidinyl]-methylamino]-6-benzothiazolol and 2-[[1-[4-(4-fluorophenoxy)butyl]-4-piperidinyl]-methylamino]-5-benzothiazolol and the pharmaceutically acceptable acid addition salts thereof.

Interesting compounds are 2-[[1-[4-(4-fluorophenoxy) butyl]-4-piperidinyl]-methylamino]-6-benzothiazolol and the pharmaceutically acceptable acid addition salts thereof.

Preferred compound is 2-[[1-[4-(4-fluorophenoxy)butyl]-4-piperidinyl]-methylamino]-6-benzothiazolol (Z)-2-butenedioate(1:1).

Procedures for the preparation of the present compounds of formula (I) have been extensively described in U.S. Pat.

No. 4,861,785. More in particular the compounds of the present invention may be prepared by art-known N-alkylation of an intermediate of formula (II), wherein $R^1$ and $R^2$ are defined as under formula (I), with a reagent of formula (III), wherein W is a reactive leaving group such as, for example, halo, e.g. chloro.

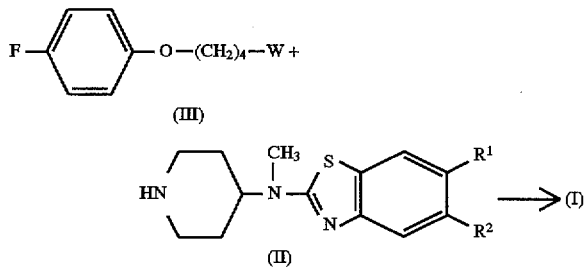

Normal heart frequency is regulated by an impulse originating from the sinus node. This sinus node impulse propagates through the heart tissue causing the atria and the ventricles to contract in a coordinated manner.

Reentry arrhythmias occur when the normal sinus node impulse activates the heart except for an area of diminished responsiveness; by the time this abnormal area is activated, the remainder of the heart has recovered, and the impulse reenters the normal zone from the abnormal area, eliciting a premature contraction. Said areas of diminished responsiveness can occur, for instance, when areas of heart tissue are damaged due to ischaemia or an infarction.

As mentioned hereinabove reentry arrhythmias can be treated or prevented by prolonging the refractory period of the cardiac cells. Said refractory period is defined as the period wherein a cardiac cell is not able to react to an incoming impulse. When an impulse originating from an abnormal zone reenters the normal zone of heart tissue while the cardiac cells are still in a state wherein an incoming impulse is not propagated, the errant signal is quenched, thus preventing the occurrence of a reentry arrhythmia.

The compounds of the present invention have unexpectedly been found to prolong the refractory period of cardiac cells and consequently they are useful as class III antiarrhythmics. Moreover, in contrast to the presently available class III antiarrhythmics, the compounds of the present invention would have less arrhythmogenic activity, more in particular, the present compounds would have less tendency to induce "torsades de pointes". These "torsades de pointes" are fibrillations that occur when the refractory period is stretched too long. The compounds of formula (I) would even have the ability to reduce the incidence of "torsades de pointes".

Prolongation of the refractory period can be measured in an electrophysiological way by measuring the prolongation of the action potential duration, which can be observed in vitro or in vivo, and is recognized on an electrocardiogram by a widening of the QTc-interval, which is the time interval between the arrival of the signal in the ventricles and the end of the signal. The pharmacological example hereinunder shows the ability of compounds of formula (I) to extend the action potential duration considerably.

The present compounds are without effect on potassium channels. Furthermore they induce a pronounced prolongation of the action potential duration in the ventricular cells and have virtually no effect on the action potential duration of the Purkinje cells.

The present compounds are potent in inhibiting lipid peroxidation and scavenging of reactive oxygen species. Lipid peroxidation is involved in ischaemic damage.

The compounds of formula (I) show a good bioavailability and are only slowly metabolized, thus ensuring a long duration of action. Moreover the present compounds are practically devoid of central effects. There is also evidence that the present compounds are useful as agents against auricular as well as ventricular arrhythmias or fibrillations.

In view of their pharmacological properties, the compounds of formula (I) can be used as a medicine to treat people suffering from arrhythmias, especially reentry arrhythmias. Said use as a medicine or method of treatment consists of administering to subjects suffering from arrhythmias, especially reentry arrhythmias, a therapeutically effective amount of a compound of formula (I).

The subject compounds may be formulated into various pharmaceutical forms for administration purposes. Said pharmaceutical forms or compositions are deemed novel and consequently constitute another aspect of the present invention. Also the preparation of said compositions constitutes a further aspect of the present invention. As appropriate compositions there may be cited all compositions usually employed for systemically or topically administering drugs. To prepare the pharmaceutical compositions of this invention, an effective amount of the particular compound, optionally in acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carders are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. As appropriate compositions for topical application there may be cited all compositions usually employed for topically administering drugs, e.g., creams, gellies, dressings, pastes, ointments, salves, powders and the like.

It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

Those of skill in the treatment of arrhythmias could easily determine the effective daily amount from the test results presented here. In general it is contemplated that an effective daily amount would be from 0.01 mg/kg to 20 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The following examples are intended to illustrate and not to limit the scope of the present invention.

EXPERIMENTAL PART

A. Preparation of Final Compounds

EXAMPLE 1

A mixture of 4.04 g of 1-(4-chlorobutoxy)-4-fluorobenzene, 5.58 g of 2-[methyl-(4-piperidinyl)amino]-5-benzothiazolol, 2.12 g of sodium carbonate and 40 ml of N,N-dimethylacetamide was stirred for 17 hours at 60° C. After cooling to room temperature, the reaction mixture was diluted with 120 ml of water. The mixture was extracted twice with methylbenzene. The combined extracts were dried, filtered and evaporated. The residue was purified by column chromatography (silica gel; CHCl$_3$/CH$_3$OH 96:4). The eluent of the desired fraction was evaporated and the residue was converted into the (Z)-2-butenedioate salt in 236 ml of 2-propanol. After cooling to room temperature, the salt was filetered off (the filtrate was set aside), washed with 2-propanol and dried overnight in vacuo at 40° C. and for 2.5 hours in vacuo at 60° C., yielding a first fraction of 7.8 parts (71.4%) of product. Evaporation of the filtrate yielded an additional fraction of 2.2 parts (20.1%) of product. Total yield: 10 parts (91.5%) of 2-[[1-[4-(4-fluorophenoxy)butyl]-4-piperidinyl]methylamino]-5-benzothiazolol (Z)-2-butenedioate (1:1); mp. 187.8° C. (comp. 1).

EXAMPLE 2

A mixture of 3.05 g of 1-(4-chlorobutoxy)-4-fluorobenzene, 4.19 g of 2-[methyl-(4-piperidinyl)amino]-6-benzothiazol, 1.6 g of sodium carbonate, 30 ml of N,N-dimethylacetamide was stirred for 20 hours in an oil bath at 60° C. After cooling, 120 ml of water was added and the mixture was extracted twice with methylbenzene. The combined extracts were washed with water and a NaCl solution, dried, filtered and evaporated. The residue was purified by column chromatography (silica gel; CHCl$_3$/CH$_3$OH 96:4). The eluent of the pure fractions was evaporated and the residue was converted into the (Z)-2-butenedioate salt in 2-propanol. The salt was filtered off (the filtrate was set aside) and dried, yielding a first fraction of 4.6 parts (45.1%) of product; mp. 107.7° C. The eluent of the less pure fractions was evaporated and the residue was converted into the (Z)-2-butenedioate salt in 2-propanol. The salt was filtered off (the filtrate was also set aside) and dried, yielding a second fraction of 2.3 parts (22.5%) of product; mp. 108.4° C. The combined filtrates were evaporated and the residue was stirred in trichloromethane. The mixture was treated with NaHCO$_3$ solution to pH 7.5–8. After stirring, the organic layer was separated, dried, filtered and evaporated. The residue was converted into the (Z)-2-butenedioate salt in 2-propanol. The salt was filtered off and dried, yielding a third fraction of 1.26 parts (12.3%) of product; mp. 114.9° C. Total yield: 8.16 parts (79.9%) of 2-[[1-[4-(4-fluorophenoxy)-butyl]-4-piperidinyl]methylamino]-6-benzothiazolol (Z)-2-butenedioate (1:2). monohydrate (comp. 2).

In a similar way there was also prepared:
2-[[1-[4-(4-fluorophenoxy)butyl]-4-piperidinyl]methylamino]-6-benzothiazolol (Z)-2-butenedioate (1:2); mp. 107.8° C. (comp. 3).

EXAMPLE 3

A mixture of 2-(methyl-4-piperidinylamino)-6-benzothiazolol dihydrobromide (0.056 mol) and sodium carbonate (0.142 mol) in N,N-dimethylacetamide (500 ml) was stirred for 1 hour at 60° C. A solution of 1-(4-chlorobutoxy)-4-fluorobenzene (0.061 mol) in N,N-dimethylacetamide (15 ml) was added and the reaction mixture was stirred overnight at 60° C. The cooled reaction mixture was poured out into ice water. This mixture was extracted with toluene. The separated organic layer was dried (MgSO4), filtered and the solvent was evaporated. The residue (30 g) was purified by column chromatography over silica gel (eluent: CH$_2$Cl$_2$/CH$_3$OH 97/3). The pure fractions were collected and the solvent was evaporated. The residue was converted into the (Z)-2-butenedioic acid salt (1:1) in 2-propanol. The precipitate was filtered off and dried, yielding 18 g (58.9%)of 2-[[1-[4-(4-fluorophenoxy)butyl]-4-piperidinyl]methylamino]- 6-benzothiazolol (Z)-2-butenedioate(1:1); mp. 180.7° C. (comp. 4).

B. Pharmacological Examples

EXAMPLE 4

The test protocol of this example is described in Archives of Pharmacology, 1985, 329, 316–325.

Guinea-pigs of either sex weighing 250–500 g were stunned and exsanguinated. Their hearts were rapidly excised and the papillary muscles were dissected. The preparations were mounted in a 2.5 ml tissue chamber and were kept in Tyrode-solution at 35° C. Internal circulation was maintained by continuous gassing with 95% O$_2$ and 5% CO$_2$. The preparations were stimulated electrically via two platinum electrodes located close to the muscle base at a frequency of 1 Hz (pulse duration 1 ms). Transmembrane potentials were measured using conventional glass microelectrodes, filled with 3 mol/l KCl. A silver/silver chloride electrode in the organ bath served as the indifferent electrode. The potential difference was recorded via a preamplifier with a capacitance compensated, high impedance input on the screen of a storage oscilloscope.

After an equilibration period of 90 minutes, the perfusion solution of the bath was switched to test compound containing solution. The biological samples were incubated with test compound containing solution during 45 minutes (the actual concentrations are shown in the table). The action potential was measured at 20%, 50% and 90% repolarization ($\Delta APD_{20}$, $\Delta APD_{50}$, $\Delta APD_{90}$). Repolarization is the process by which a cell, after it reached its maximum value, returns to the resting membrane potential.

TABLE

Test compound is compound 2.

| | Concentration | |
|---|---|---|
| | 0.3 µmol/l | 1.0 µmol/l |
| $\Delta APD_{20}$ | 4.3 ± 12.1 ms | 6.0 ± 13.6 ms |
| $\Delta APD_{50}$ | 16.4 ± 6.7 ms | 19.1 ± 7.8 ms |
| $\Delta APD_{90}$ | 19.8 ± 6.2 ms | 23.9 ± 7.1 ms |

EXAMPLE 5

The test protocol of this example is described in Journal of Cardiovascular Pharmacology, 1992, p. 682.

In a series of anaesthetized dogs in which prior to the actual experiments with the test compound a myocardial infarction had been induced by occlusion of a major coronary artery, compound 4 reduced in 5 out of 7 animals the incidence of sustained ventricular tachycardia elicited by a programmed electrical stimulation of the heart of doses of 0.32 mg/kg and 0.48 mg/kg when administered intravenously. At the said doses, compound 4 produced a substantial prolongation of the effective refractory period (16% after 0.32 mg/kg given innavenously) and a comparatively small prolongation of QTc-interval (+4% after 0.32 mg/kg).

EXAMPLE 6

In nine anaesthetised dogs a chronic atrioventricular node-block was created and epicardial electrodes were positioned on the left ventricular apex en right ventricular basis. After 14 to 80 days, dogs under anaesthesia were repetitively subjected to a test protocol consisting of a combination of bradycardia (caused by the atrioventricular node-block), a programmed electrical stimulation protocol (8 regular beats followed by a short-long-short interval) and presence of the compound to be investigated. The monophasic action potential was recorded in the left and fight ventricle, together with an EGG recording. A "torsade de pointes"-arrhythmia was defined as a ventricular tachycardia for $\geq 5$ beats wich terminates spontaneously or requires cardioversion, and which can be induced $\geq 3$ times with the same pacing protocol. Under these conditions, "torsade de pointes"-arrhythmias could not be elicited in the presence of compound 4 at doses of 0.32 and 0.48 mg/kg i.v. Only when the dose was increased ($\geq 0.63$ mg/kg i.v.) arrhythmias could by induced in just 33% of the dogs. These results show that compound 4 is much less pro-arrhythmogenic than currently available class-III drugs.

C. Composition Examples

"Active ingredient" (A.I.) as used throughout these examples relates to a compound of formula (I), a pharmaceutically acceptable acid addition salt or a stereochemically isomeric form thereof.

EXAMPLE 7

Oral Drops

500 Grams of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.L The resulting solution was filled into suitable containers.

EXAMPLE 8

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 9

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

EXAMPLE 10

Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hyarogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE 11

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration (U.S.P. XVII p. 811) and filled in sterile containers.

EXAMPLE 12

Suppositories

3 Grams A.I. was dissolved in a solution of 3 grams 2,3-dihydroxybutanedioic acid in 25 ml polyethylene glycol 400. 12 Grams surfactant (SPANS®) and triglycerides (Witepsol 555®) q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

EXAMPLE 13

Injectable Solution

60 Grams of A.I. and 12 grams of benzylalcohol were mixed well and sesame oil was added q.s. ad 1 l, giving a solution comprising 60 mg/ml of A.I. The solution was sterilized and filled in sterile containers.

We claim:

1. A method of treating subjects suffering from arrhythmia which comprises administering to such subjects a therapeutically effective amount of a compound of the formula:

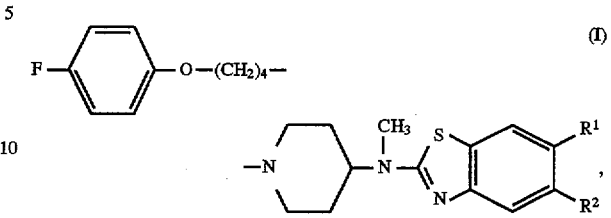

wherein one of the variables $R^1$ and $R^2$ is hydroxy, while the other is hydrogen, and the pharmaceutically acceptable acid addition salts thereof.

2. The method of claim 1 wherein the compound is 2-[[1-[4-(4-fluorophenoxy)butyl]-4-piperidinyl] methylamino]-5-benzothiazolol or a pharmaceutically acceptable acid addition salt thereof.

3. The method of claim 1 wherein the compound is 2-[[1-[4-(4-fluorophenoxy)butyl]-4-piperidinyl] methylamino]-6-benzothiazolol or a pharmaceutically acceptable acid addition salt thereof.

4. The method of claim 1 wherein the compound is 2-[[1-[4-(4-fluorophenoxy)butyl]-4-piperidinyl] methylamino]-6-benzothiazolol (Z)-2-butenedioate(1:1).

* * * * *